(12) United States Patent
Grammenos et al.

(10) Patent No.: US 6,417,388 B1
(45) Date of Patent: Jul. 9, 2002

(54) METHOD FOR PRODUCING ALKENYL-SUBSTITUTED BIS(OXIME ETHER) DERIVATIVES

(75) Inventors: Wassilios Grammenos, Ludwigshafen; Hubert Sauter, Mannheim; Andreas Gypser, Mannheim; Herbert Bayer, Mannheim; Norbert Götz, Worms; Roland Götz, Neulussheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,412

(22) PCT Filed: Nov. 12, 1999

(86) PCT No.: PCT/EP99/08740

§ 371 (c)(1),
(2), (4) Date: May 9, 2001

(87) PCT Pub. No.: WO00/31023

PCT Pub. Date: Jun. 2, 2000

(30) Foreign Application Priority Data

Nov. 20, 1998 (DE) ......................... 198 53 704

(51) Int. Cl.$^7$ ............................. C07C 229/00
(52) U.S. Cl. ........................ 560/35; 564/133
(58) Field of Search ............. 560/35; 564/199, 564/133, 149

(56) References Cited

U.S. PATENT DOCUMENTS 5,981,585 A * 11/1999 Ziegler et al.

* cited by examiner

Primary Examiner—Gary Geist
Assistant Examiner—Paul A. Zucker
(74) Attorney, Agent, or Firm—Keil & Weinkauf

(57) ABSTRACT

The process for preparing alkenyl-substituted bis(oxime ether) derivatives of the formula I

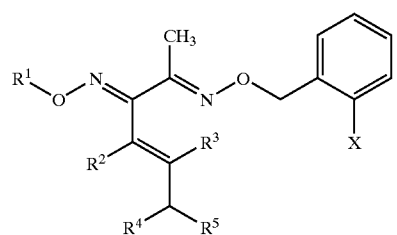

where:

- $R^1$ is unsubstituted $C_1-C_4$-alkyl or $C_2-C_4$-alkenyl-, $C_2-C_4$-alkynyl- or phenyl-substituted methyl;
- $R^2$, $R^4$ independently of one another are hydrogen or methyl;
- $R^3$, $R^5$ independently of one another are hydrogen or $C_1-C_4$-alkyl, trifluoromethyl or phenyl and
- X is —C(=CHCH$_3$)—COOCH$_3$,
  —C(=CHOCH$_3$)—COOCH$_3$,
  —C(=NOCH$_3$)—COOCH$_3$,
  —C(=NOCH$_3$)—CONHCH$_3$ or
  —N(OCH$_3$)—COOCH$_3$, and intermediates which are obtainable by this process are described. Alkenyl-substituted bis(oxime ether) derivatives of the formula I are described in the literature as interesting crop protection agents.

3 Claims, No Drawings

METHOD FOR PRODUCING ALKENYL-SUBSTITUTED BIS(OXIME ETHER) DERIVATIVES

This application is a 371 of PCT1EP99/08740 filed Nov. 12, 1999.

1. Field of the Invention

The present invention relates to a process for preparing alkenyl-substituted bis(oxime ether) derivatives of the formula

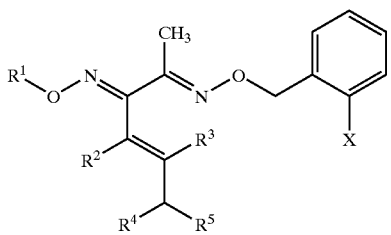

I where:
- $R^1$ is unsubstituted $C_1$–$C_4$-alkyl or $C_2$–$C_4$-alkenyl-, $C_2$–$C_4$-alkynyl- or phenyl-substituted methyl;
- $R^2$,$R^4$ independently of one another are hydrogen or methyl;
- $R^3$,$R^5$ independently of one another are hydrogen or $C_1$–$C_4$-alkyl, trifluoromethyl or phenyl and
- X is —C(=CHCH$_3$)—COOCH$_3$,
  —C(=CHOCH$_3$)—COOCH$_3$,
  —C(=NOCH$_3$)—COOCH$_3$,
  —C(=NOCH$_3$)—CONHCH$_3$ or
  —N(OCH$_3$)—COOCH$_3$.

2. Background of the Invention

Alkenyl-substituted bis(oxime ether) derivatives of the formula I are described in the literature as interesting crop protection agents [cf. WO-A 95/21153, WO-A 95/21154, WO-A 96/16030 and WO-A 97/03057].

If the preparation processes described in these publications are applied specifically for synthesizing the alkenyl-substituted bis(oxime ether) derivatives of the formula I, the following difficulties are encountered:

The synthesis route shown in scheme 1, where the component A of the side chain and the component B which contains the pharmacophor are built up separately and only joined at the end, fails owing to the poor accessibility of component A. In the route shown in scheme A, for example, A is inaccessible because of the high ring-closure tendency of the precursors (cf. Tetrahedron Let. (1981) 2557).

Scheme 1

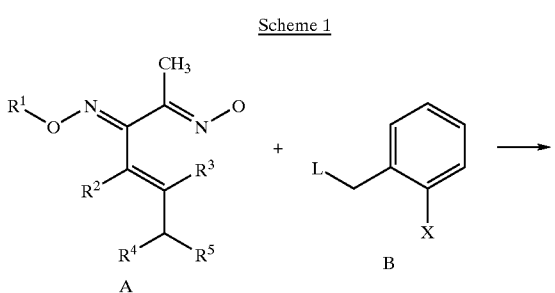

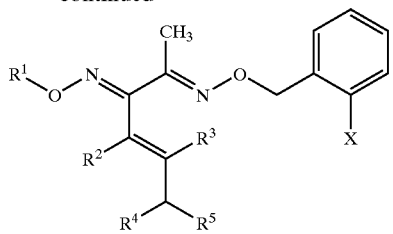

WO-A 95/21153
WO-A 95/21154
WO-A 97/03057
WO-A 96/16030

Scheme A:

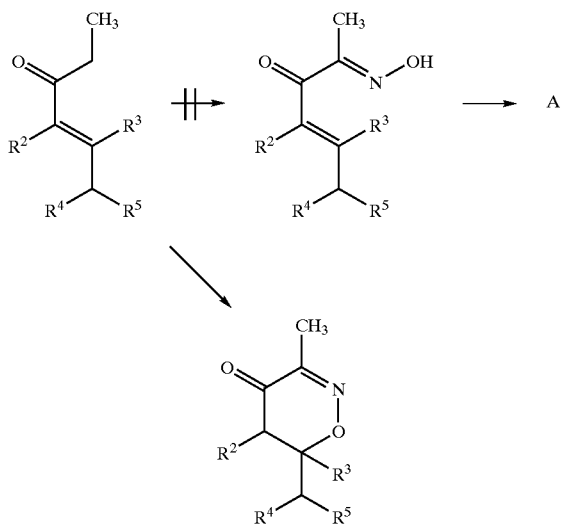

It would furthermore be feasible to build up the side chain successively, starting from building block B, but this has the disadvantage that a large number of synthesis steps have to be performed successively. The expected total yield in such a process is only moderate, and the process is furthermore very tedious.

BRIEF SUMMARY OF THE INVENTION

It is an object of the present invention to provide an economical process which affords alkenyl-substituted bis (oxime ether) derivatives of the formula I in good yield starting from easily accessible starting materials.

We have found that this object is achieved by the process mentioned at the outset which comprises rearranging an alkenylalkyl derivative of the formula II,

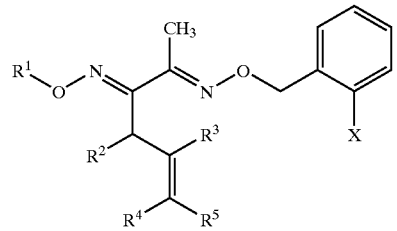

II in which the substituents $R^1$ to $R^5$ and X are as defined above, using a base and/or an isomerization catalyst.

DETAILED DESCRIPTION OF THE INVENTION

As shown in scheme 2, compounds of the formula II can be obtained in an advantageous manner starting from a bis(oxime) monoether of the formula IV and a benzyl derivative of the formula III.

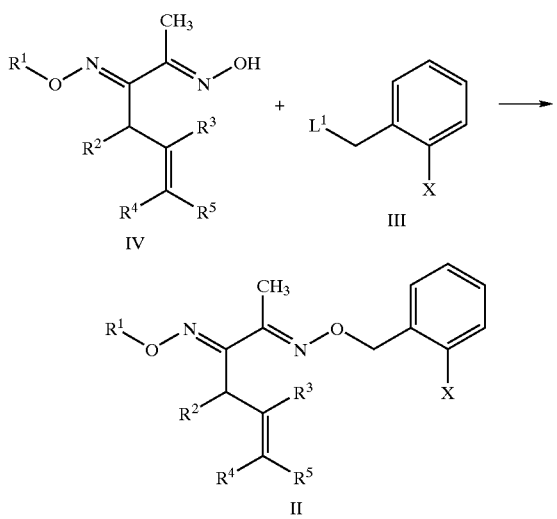

Scheme 2:

The synthesis strategy shown in scheme 3 has been found to be particularly advantageous for compounds I having an oxime ether amide pharmacophor.

The process according to the invention is illustrated in more detail below.

The isomerization can be carried out in the presence of a base and/or an isomerization catalyst.

Suitable bases are metal hydrides, such as, for example, sodium hydride, or in particular alkali metal alkoxides, such as, for example, potassium tert-butoxide and preferably sodium methoxide or potassium methoxide.

In general, the base is employed in a molar ratio of from 1 to 4 and preferably from 1 to 2, based on the starting material II.

In addition or alternatively to the base, it is also possible to use an isomerization catalyst.

Suitable isomerization catalysts are, in particular, metallic palladium, or else palladium salts, such as palladium(II) chloride or palladium(II) acetate.

The isomerization catalyst is usually employed in a concentration of from 0.1 to 5 mol %.

Suitable solvents are, for example, aliphatic or aromatic hydrocarbons, such as toluene, xylene, heptane, aliphatic or cyclic ethers, such as 1,2-dimethoxyethane, tetrahydrofuran, dioxane or, in particular, polar aprotic solvents, such as acetonitrile, dimethyl sulfoxide, sulfolane, dimethyl formamide or dimethyl acetamide.

The reaction temperature is generally from 20 to 120° C. and preferably 20–40° C. In the case of the palladium-catalyzed reaction, higher temperatures of from 20 to 160° C. and preferably of from 80 to 140° C. are used.

The starting materials for the isomerization reaction are compounds of the formula II which are preferably prepared,

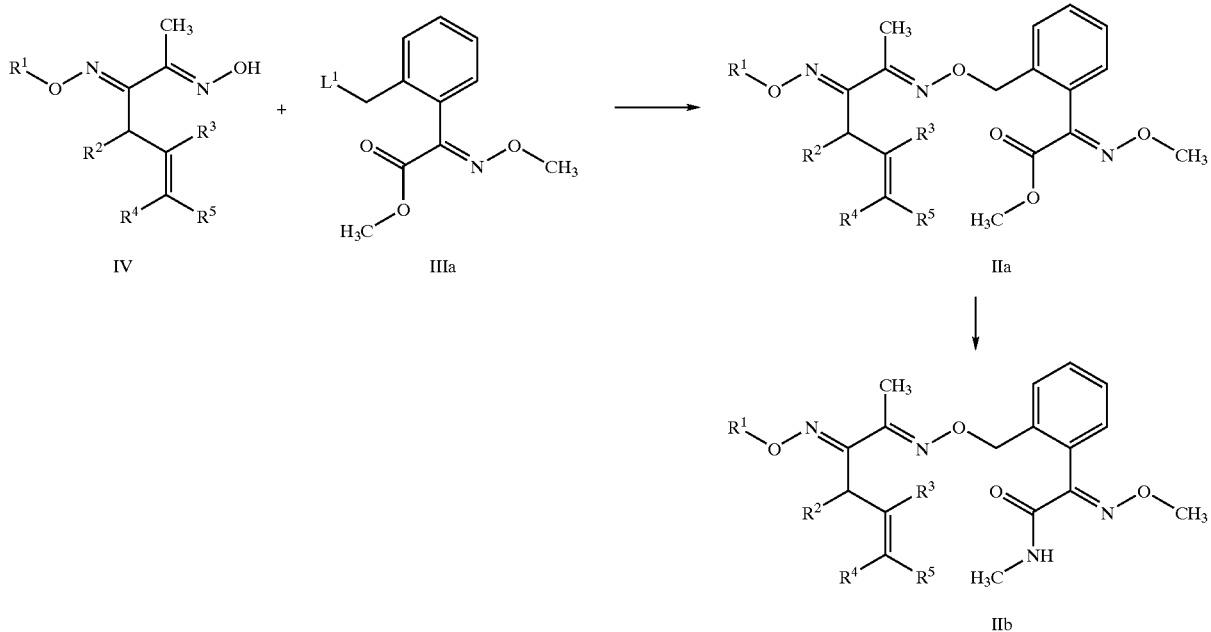

Scheme 3

By alkylating compound IV with compound IIIa, the oxime ether ester IIa is obtained, which can be converted into the corresponding amide IIb. In the last step, the double bond is isomerized, giving the oxime ether amides of the formula I.

as shown in scheme 2a, by route A) starting from a bis (oxime) monoether of the formula IV and a benzyl derivative of the formula III, or by route B) starting from an oxime ether of the formula V and a hydroxylamine of the formula VI.

Scheme 2a

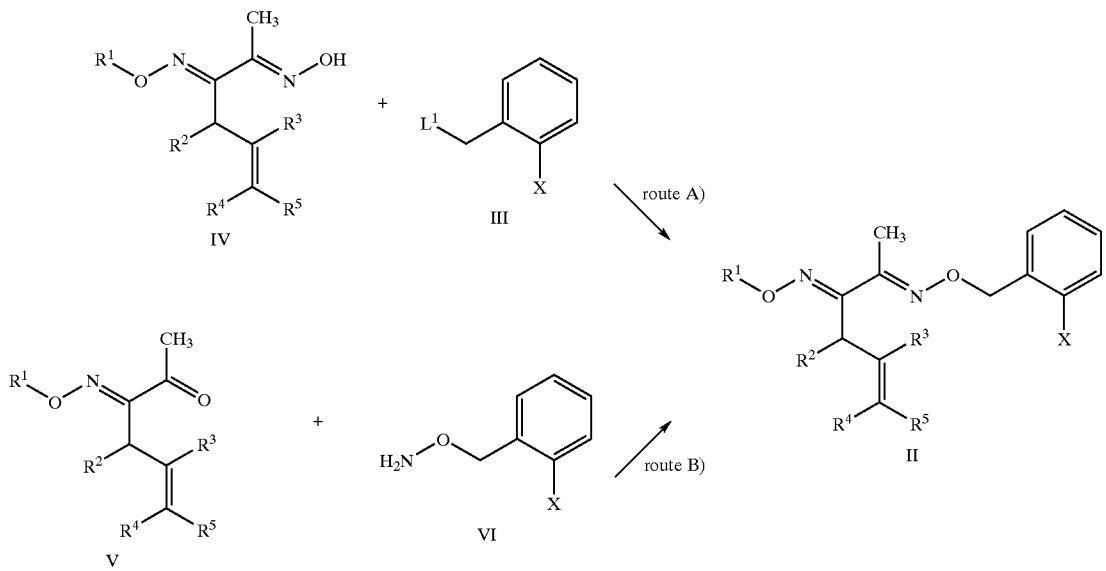

The reaction A) is a nucleophilic substitution which can be carried out under the customary reaction conditions. The benzyl compounds III are to be understood as compounds in which X is as defined in claim 1 and $L^1$ is a leaving group, such as halogen, acyloxy, alkylsulfonyloxy or arylsulfonyloxy and in particular chlorine or bromine. The substituents $R^1$ to $R^5$ of the bis(oxime) monoethers of the formula IV are as defined in claim 1.

The reaction is expediently carried out in an inert solvent such as an ether, for example tetrahydrofuran or dioxane, or in a polar aprotic solvent, for example acetone, acetonitrile, dimethyl sulfoxide, sulfolane, dimethylformamide or dimethylacetamide.

The base which is employed is usually sodium carbonate or potassium carbonate, sodium hydride, sodium methoxide or a tertiary amine.

The reaction temperature is usually from −20 to 80° C.

The reaction can also be carried out in a two-phase system (for example dichloromethane/water) with the aid of a suitable phase-transfer catalyst.

Work-up of the reaction mixtures can be carried out, for example, by extraction.

The benzyl compounds of the formula III are disclosed in EP-A 348766, EP-A 363818 and EP-A 624155.

An advantageous route for preparing the starting materials IV and V is shown in scheme 4.

Scheme 4

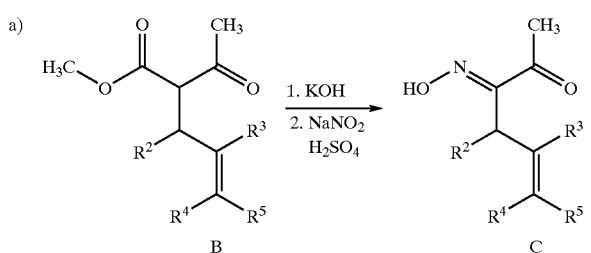

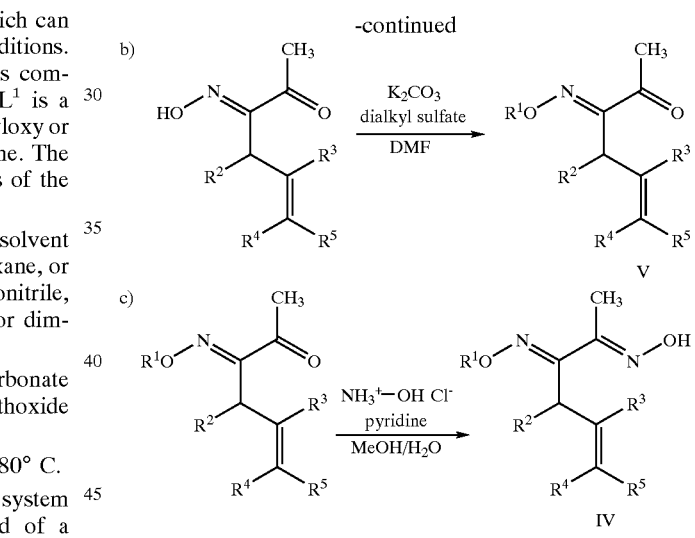

Step a):

Step a) is carried out similarly to the procedure described in U.S. Pat. No. 4,707,484.

Suitable for use as solvents are alcohols, such as, for example, methanol, and, in particular, water. In certain cases it may be advantageous to add solubilizers, such as, for example, surfactants or ethylene glycol.

Suitable bases are, in particular, sodium hydroxide and potassium hydroxide, which are usually employed in equimolar amounts or in an excess of up to 10 mol, based on the acetoacetic ester B. Nitrite is to be understood as meaning, for example, an alkali metal nitrite, in particular sodium nitrite, which is usually employed in equimolar amounts or in an excess of up to 30 mol %, based on the acetoacetic ester B.

In general, the reaction temperature should not exceed 40° C., since otherwise undesirable side reactions may occur. In water, the reaction is therefore preferably carried out at from −20 to 40° C., in particular at from 0 to 15° C.

After a period of from 10 to 48 hours, the reaction mixture usually becomes clear. It is then adjusted to a pH of from 0 to 5 and preferably from 1 to 3 using an acid, such as, for example, hydrochloric acid or sulfuric acid.

Work-up is carried out by customary methods, for example by extraction. For purification, the oxime can, for example, be converted into the corresponding salt using bases and reprecipitated using an acid.

The acetoacetic ester B used in the reaction can be prepared as described in Tetrahedron (1985)4633 (see scheme 5)

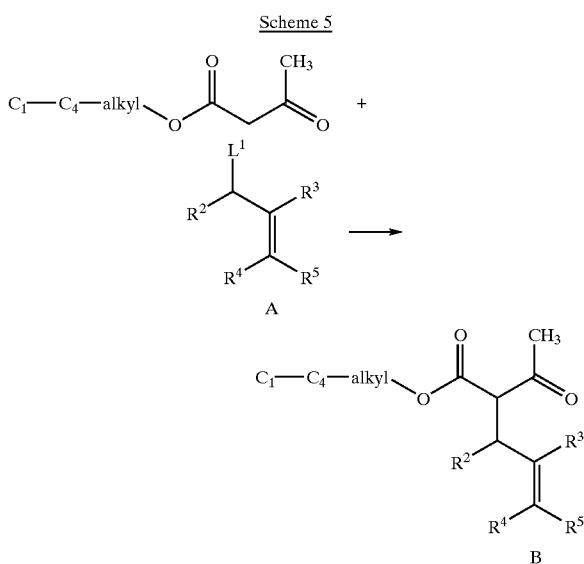

Scheme 5

The alkenylalkyls of the formula A in which $R^2$ to $R^5$ are as defined in claim 1 and $L^1$ is halogen, acyloxy, alkylsulfonyloxy or arylsulfonyloxy are known, or they can be synthesized by processes known from the literature (Z. Org. Khim. (1997) 486; Bull. Chem. Soc. Jpn. (1980) 2586; J. Am. Chem. Soc. (1984) 2211; J. Am. Chem. Soc. (1960) 1886; DE-A 19 556 66; DE-A 33 173 56; EP-A 271212; Tetrahedron Let. (1986) 6027; Tetrahedron Let. (1994) 1371 and 2679; J. Fluorine Chem. (1997) 67; Helv. Chim. Acta (1951) 1514; Organomet. Chem. (1985) 395).

Step b):

The alkylation is usually carried out in the presence of an inert organic solvent. Suitable solvents are, inter alia, aliphatic or aromatic hydrocarbons, such as, for example, toluene, xylene, heptane or cyclohexane, aliphatic or cyclic ethers, such as, for example, 1,2-dimethoxyethane, tetrahydrofuran or dioxane. Preference is given to using polar aprotic solvents: ketones, such as, for example, acetone, nitriles, such as, for example, acetonitrile, amides, such as, for example, dimethylformamide, dimethylacetamide or N-methylpyrrolidone, or ureas, such as tetramethylurea.

The alkylating agent used is usually a halide, preferably a chloride or bromide, a sulfate, preferably dimethyl sulfate, a sulfonate, preferably a methanesulfonate (mesylate) or a toluenesulfonate (tosylate)

The amount of base or alkylating agent is preferably from one to two times the equimolar amount, based on the compound V.

The reaction is usually carried out in the presence of an inorganic base, such as sodium hydroxide or potassium hydroxide, sodium carbonate or potassium carbonate, sodium bicarbonate or potassium bicarbonate, or of an alkali metal alkoxide, such as sodium methoxide or potassium tert-butoxide.

The reaction temperature is generally between 0° C. and 50° C., preferably between 0° C. and 40° C. and in particular at room temperature.

Work-up can be carried out, for example, by extraction.

To remove residual amounts of alkylating agent, it may be advantageous to wash the reaction batch with ammoniacal solution, for example.

Step c):

Hydroxylamine is employed either in the form of an acid addition salt or as free base, it being possible to liberate the latter from the salt by addition of a strong base.

Preference is given to using the acid addition salts of hydroxylamine. All customary acids are suitable for preparing the acid addition salts. Below, only some acids are mentioned, by way of example: carboxylic acids, such as acetic or propionic acid, dicarboxylic acids, such as oxalic or succinic acid, mineral acids, such as phosphoric or carbonic acid and in particular hydrochloric acid or sulfuric acid.

If the acid addition salts of hydroxylamine are employed, it is enerally advantageous to add a base to bind the acid liberated in the reaction. In many cases, a pH of from 3 to 7 and in articular of from 4 to 6 has been found to be advantageous for the oximation. Side reactions such as ring-closure reactions may occur outside of these pH ranges.

In general, from 1 to 2.5 molar equivalents of a base are added. Suitable bases are, in particular, pyridines, trialkylamines, sodium hydroxide, sodium acetate and sodium methoxide. If sodium acetate is used, it is customary to add glacial acetic acid.

Conversely, it is of course also possible to employ the hydroxylamine as free base and to use one of the abovementioned acids to set the abovementioned pH range.

Suitable solvents are, for example, the solvents described in the previous step. In addition, carboxylic acids, such as acetic acid, or else water/pyridine mixtures are also suitable. Particularly suitable are alcohols, such as methanol, ethanol, n-propanol or isopropanol, and mixtures of these with water and/or pyridine.

The reaction temperature is usually from −20 to 50° C., preferably from 0 to 40° C. and in particular from 20 to 25° C.

The work-up of the reaction mixture is preferably carried out by extraction, as described in the previous step. To remove the base completely, it may be advantageous to wash the crude product first, with a dilute aqueous acid and then with water.

Route B) shown in scheme 2a can be carried out similarly to the procedure described in J. Chem. Soc, Chem. Commun. 1986, 903. The preparation of the oxime ethers V is described above; the hydroxylamines of the formula VI are disclosed in EP-A 244786.

PREPARATION EXAMPLES

Preparation of the intermediates IV and v

Example 1

Preparation of 5-methylhex-5-en-2,3-dione 3-oxime

At 10° C., 200 g of methyl 2-acetyl-4-methylpent-4-enoate (Preparation: cf. Tetrahedron (1985) 4633) in 2000 ml of aqueous 10% strength potassium hydroxide solution were admixed with 85 g of sodium nitrite, and the mixture was stirred at 23° C. for 18 hours. With ice-cooling, 1000 ml of 10% strength sulfuric acid were subsequently added dropwise such that the internal temperature remained below 10° C. The mixture was then stirred at 10° C. until evolution of $CO_2$ had ceased. For work-up, the mixture was extracted with methyl tert-butyl ether, the combined organic phases were extracted with 3 N aqueous sodium hydroxide solution and the alkaline phases were adjusted to pH 1 using 20% strength sulfuric acid. They were then extracted with methylene chloride, the extract was dried over sodium sulfate and the solvent was removed under reduced pressure. This gave 142 g of the title compound as a yellow oil which crystallized on standing.

$^1$H NMR (CDCl$_3$, ppm): δ=4.8 (1H); 4.6 (1H); 3.3 (2H); 2.4 (3H); 1.8 (3H). Preparation of the mono(oxime ethers) V.

Example 2

Preparation of 5-methylhex-5-ene-2,3-dione 3-(O-methyloxime)

141 g of 5-methylhex-5-ene-2,3-dione 3-oxime from Example 1 were dissolved in 750 ml of acetone and admixed with 165.6 g of potassium carbonate. 145 g of dimethyl sulfate in 100 ml of acetone were then added dropwise, and the mixture was stirred at 23° C. for 4 hours. The solvent was then removed under reduced pressure, the residue was taken up in methyl tert-butyl ether/water and the aqueous phase was extracted repeatedly with methyl tert-butyl ether. The combined organic phases were washed with 15% strength ammonia solution and water and dried over sodium sulfate, and the solvent was removed under reduced pressure. This gave 141 g of the title compound as a yellow oil.

$^1$H NMR (CDCl$_3$, ppm): δ=4.77 (1H); 4.57 (1H); 4.0 (3H); 3.2 (2H).

Example 3

Preparation of 5-methylhex-5-ene-2,3-dione 3-(O-ethyloxime)

285.7 g of 5-methylhex-5-ene-2,3-dione 3-oxime from Example 1 were dissolved in 750 ml of acetone and admixed with 335.8 g of potassium carbonate. 362 g of diethyl sulfate in 300 ml of acetone were then added dropwise, and the mixture was stirred at 23° C. for 2 hours. The solvent was then removed under reduced pressure, the residue was taken up in methyl tert-butyl ether/water and the aqueous phase was extracted repeatedly with methyl tert-butyl ether. The combined organic phases were washed with 15% strength ammonia solution and water and dried over sodium sulfate, and the solvent was removed under reduced pressure. This gave 355.4 g of the title compound as a yellow oil.

$^1$H NMR (CDCl$_3$, ppm): δ=4.8 (1H); 4.6 (1H); 4.3 (2H); 3.2 (2H); 2.4 (3H); 1.7 (3H); 1.3 (3H). Preparation of the bis(oxime) monoethers IV.

Example 4

Preparation of 5-methylhex-5-en-2,3-dione 3-(O-methyloxime) 2-oxime 283.4 g of 5-methylhex-5-ene-2,3-dione 3-(O-methyloxime) in 800 ml of methanol were added dropwise to the solution of 140.6 g of hydroxylammonium chloride in 400 ml of water and 216.7 g of pyridine, and the mixture was stirred at 23° C. for 3 hours. The solvent was then removed under reduced pressure and the residue was poured into ice-water. The pH was subsequently adjusted to 1 using 20% strength sulfuric acid, and the precipitated product was filtered off with suction, taken up in methyl tert-butyl ether and washed with water. The organic phase was then dried over sodium sulfate and the solvent was removed under reduced pressure. This gave 266 g of the title compound as a colorless solid.

$^1$H NMR (CDCl$_3$, ppm): δ=9.3 (1H); 4.8 (1H); 4.6 (1H); 4.0 (3H); 3.3 (2H).

Example 5

Preparation of 5-methylhex-5-ene-2,3-dione 3-(O-ethyloxime)-2-oxime

By the method of Example 4, 211.3 g of hydroxylammonium chloride in 400 ml of water and 240 g of pyridine were reacted with 342.4 g of 5-methylhex-5-ene-2,3-dione 3-(O-ethyloxime) in 800 ml of methanol. This gave 305 g of the title compound as a yellowish solid.

$^1$H NMR (CDCl$_3$, ppm): δ=9.4 (1H); 4.8 (1H); 4.6 (1H); 4.2 (2H); 3.3 (2H); 2.1 (3H); 1.8 (3H); 1.3 (3H).

Compounds of the Formula II

Example 6

Preparation of 2-methoxyimino-2-[2-(2-methoxyimino-1,4-dimethyl-pent-4-enylideneaminooxymethyl)phenyl]-N-methylacetamide

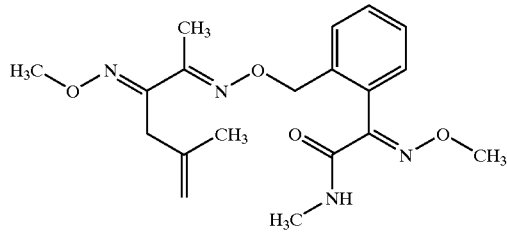

141 g of a 30% strength methanolic solution of sodium methoxide were added to 133.2 g of 5-methylhex-5-ene-2,3-dione 3-(O-methyloxime) 2-oxime (Example 4) in 150 ml of DMF, and the mixture was stirred at 23° C. for 30 minutes. 246 g of methyl (2-bromomethylphenyl)methoxyiminoacetate (preparation: see U.S. Pat. No. 4,999,042) in 400 ml of DMF were subsequently added dropwise (temperature increase to up to 50° C.), and the mixture was stirred at 23° C. for one hour. 607 g of 40% strength aqueous methylamine solution were then added dropwise and the reaction solution was stirred at 23° C. for 1 hour and then poured into ice-water/n-pentane. The mixture was subsequently stirred for 1 hour and the product was filtered off with suction, washed with water and a little n-pentane and dried under reduced pressure. Yield: 216 g of the title compound.

$^1$H NMR (CDCl$_3$, ppm): δ=6.7 (1H); 5.05 (2H); 4.7 (1H); 4.5 (1H); 4.0 (3H); 3.95 (3H); 3.3 (2H).

Example 7

Preparation of methyl 3-methoxy-2-[2-(2-methoxyimino-1,4-dimethylpent-4-enylideneaminooxymethyl)-phenyl]acrylate

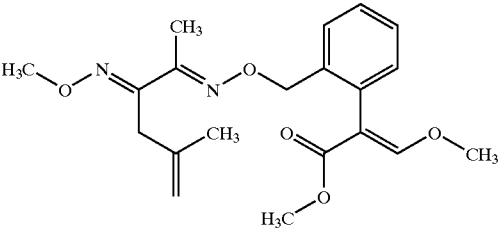

112.2 g of a 30% strength methanolic solution of sodium methoxide were added to 11.5 g of 5-methylhex-5-ene-2,3-dione 3-(O-methyloxime) 2-oxime from Example 4 in 55 ml of DMF, and the mixture was stirred at 23° C. for 30 minutes. 21.3 g of methyl 2-(2-bromomethylphenyl)-3- methoxyacrylate (preparation: see U.S. Pat. No. 5,286,894) in 400 ml of DMF were subsequently added dropwise (temperature increase to up to 35° C.), and the reaction solution was stirred at 23° C. for one hour and then poured into ice-water/n-pentane. The mixture was subsequently stirred for one hour and the product was filtered off with suction, washed with water and a little n-pentane and dried under reduced pressure. Yield: 16.7 g of the title compound as a yellowish solid.

$^{1}$H NMR (CDCl$_3$, ppm): δ=5.1 (2H); 4.7 (1H); 4.5 (1H); 3.9 (3H); 3.8 (3H); 3.7 (3H); 3.3 (2H).

Example 8

Preparation of 2-[2-(2-ethoxyimino-1,4-dimethylpent-4-enylidene-aminooxymethyl)phenyl]-2-methoxyimino-N-methyl acetamide

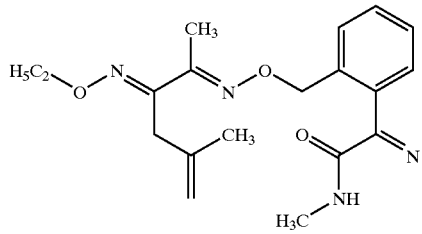

97.8 g of a 30% strength methanolic solution of sodium methoxide were added to 100 g of 5-methylhex-5-ene-2,3-dione 3-(O-ethyloxime) 2-oxime from Example 5 in 150 ml of DMF, and the mixture was stirred at 23° C. for 30 minutes. 171 g of methyl (2-bromomethylphenyl) methoxyimino acetate (preparation: see U.S. Pat. No. 4,999,042) in 400 ml of DMF were subsequently added dropwise (temperature increase to up to 50° C.), and the mixture was stirred at 23° C. for one hour. 421 g of 40% strength aqueous methylamine solution were then added dropwise and the reaction solution was stirred at 23° C. for 1 hour and then poured into ice-water/n-pentane. The mixture was subsequently stirred for one hour and the product was filtered off with suction, washed with water and a little n-pentane and dried under reduced pressure. Yield: 196 g of the title compound.

$^{1}$H NMR (CDCl$_3$, ppm): δ=1.25 (3H); 1.7 (3H); 2.0 (3H); 2.85 (3H); 3.3 (2H); 4.0 (3H); 4.2 (2H). Compounds of the formula I (Isomerization step).

Example 9

Preparation of 2-methoxyimino-2-[2-(2-methoxyimino-1,4-dimethyl-pent-3-enylideneaminooxymethyl)phenyl]-N-methyl acetamide

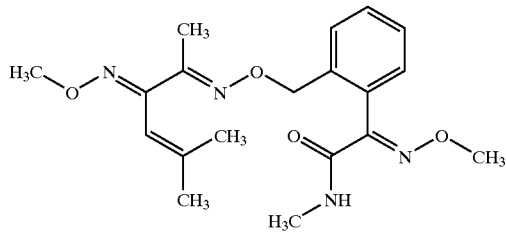

34.7 g of solid sodium methoxide in 250 ml of DMF were stirred at 23° C. for 3 hours and 120 g of the amide from Example 6 in 250 ml of DMF were then added dropwise (temperature increase to up to 30° C.). The mixture was subsequently stirred at 23° C. for 12 hours and then worked-up as in Example 6. This gave 108 g of the title compound as a colorless solid which, according to NMR, GC and HPLC analysis, contains approximately 10% of the starting material (Example 6).

$^{1}$H NMR (CDCl$_3$, ppm): δ=6.7 (1H); 5.7 (1H); 5.0 (2H); 3.9 (3H); 2.9 (3H).

Example 10

Preparation of methyl 3-methoxy-2-[2-(2-methoxyimino-1,4-dimethylpent-3-enylideneaminooxymethyl)phenyl] acrylate

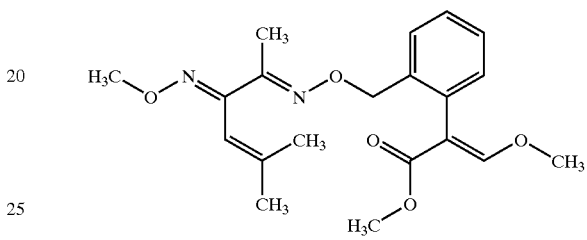

4.9 g of solid sodium methoxide were added to 16.7 g of methyl 3-methoxy-2-[2-(2-methoxyimino-1,4-dimethylpent-4-enylideneamino-oxymethyl)phenyl]acrylate from Example 7, and the mixture was stirred at 23° C. for 1 hour. Work-up was carried out similarly to Example 6. Chromatographic purification over silica gel using cyclohexane/methyl tert-butyl ether (9:1) gave 7.1 g of the title compound as a colorless solid.

IR (cm$^{-1}$): 1697, 1624, 1256, 1100, 860, 771 M.p.: 48–52° C.

Example 11

Preparation of 2-[2-(2-ethoxyimino-1,4-dimethylpent-3-enylidene-aminooxymethyl)phenyl]-2-methoxyimino-N-methylacetamide

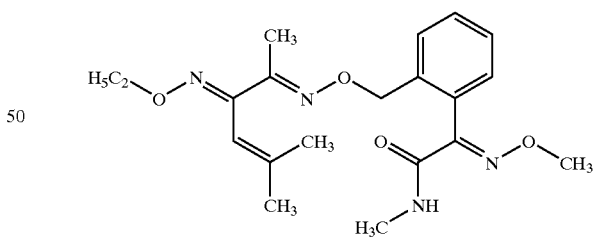

48.4 g of solid sodium methoxide in 400 ml of DMF were stirred at 23° C. for 3 hours, and 174 g of the amide from Example 8 in 250 ml of DMF were then added dropwise. The mixture was subsequently stirred at 23° C. for 18 hours and then worked-up similarly to Example 6. This gave 154 g of the title compound as a colorless solid which, according to NMR, GC and HPLC analysis, contained approximately 12% of the starting material (Example 8).

$^{1}$H NMR (CDCl$_3$, ppm): δ=6.7 (1H); 5.7 (1H); 5.1 (2H); 4.2 (2H); 3.95 (3H).

We claim:

1. A process for preparing alkenyl-substituted bis(oxime ether) derivatives of the formula I,

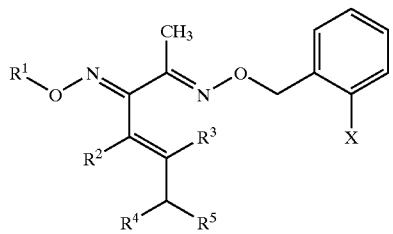

where:
- $R^1$ is unsubstituted $C_1$–$C_4$-alkyl or $C_2$–$C_4$-alkenyl-, $C_2$–$C_4$-alkynyl- or phenyl-substituted methyl;
- $R^2, R^4$ independently of one another are hydrogen or methyl;
- $R^3, R^5$ independently of one another are hydrogen or $C_1$–$C_4$-alkyl, trifluoromethyl or phenyl and
- X is —C(=CHCH$_3$)—COOCH$_3$,
  —C(=CHOCH$_3$)—COOCH$_3$,
  —C(=NOCH$_3$)—COOCH$_3$,
  —C(=NOCH$_3$)—CONHCH$_3$ or
  —N(OCH$_3$)—COOCH$_3$, which comprises rearranging an alkenylalkyl derivative of the formula II,

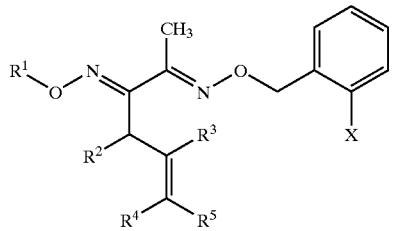

in which the substituents $R^1$ to $R^5$ and X are as defined above, using a base and/or an isomerization catalyst.

2. A process as claimed in claim 1, wherein the alkenylalkyl derivative of the formula II is prepared by reacting a benzyl compound of the formula III,

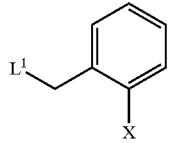

in which the substituent X is as defined in claim 1 and $L^1$ is halogen, acyloxy, alkylsulfonyloxy or arylsulfonyloxy with a bisoxime monoether of the formula IV,

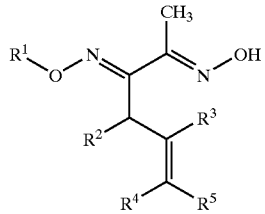

in which the substituents $R^1$ to $R^5$ are as defined in claim 1 in an inert organic solvent in the presence of a base.

3. A process as claimed in claim 2, wherein the alkenylalkyl derivative of the formula IIb,

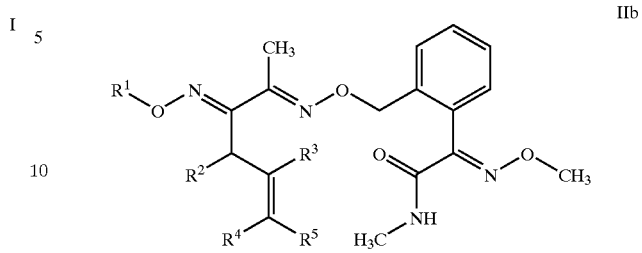

where:
- $R^1$ is unsubstituted $C_1$–$C_4$-alkyl or $C_2$–$C_4$-alkenyl-, $C_2$–$C_4$-alkynyl- or phenyl-substituted methyl;
- $R^2, R^4$ independently of one another are hydrogen or methyl;
- $R^3, R^5$ independently of one another are hydrogen or $C_1$–$C_4$-alkyl, trifluoromethyl or phenyl and
- X is —C(=CHCH$_3$)—COOCH$_3$,
  —C(=CHOCH$_3$)—COOCH$_3$,
  —C(=NOCH$_3$)—COOCH$_3$,
  —C(=NOCH$_3$)—CONHCH$_3$ or
  —N(OCH$_3$)—COOCH$_3$, is obtained by reacting a benzyl compound of the formula IIIa,

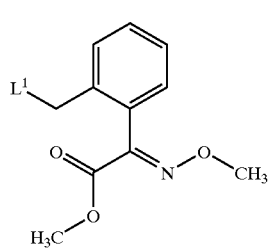

in which $L^1$ is halogen, acyloxy, alkylsulfonyloxy or arylsulfonyloxy with a bisoxime monoether IV which is as defined in claim 2 to give the alkenylalkyl derivative of the formule IIa,

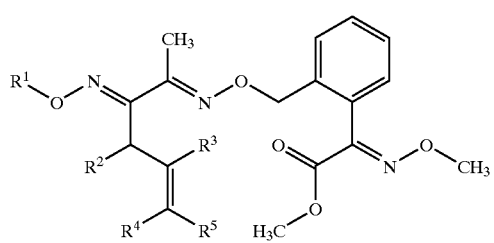

followed by reaction of IIa with methylamine.

* * * * *